United States Patent
Kirkpatrick et al.

(10) Patent No.: US 8,889,169 B2
(45) Date of Patent: *Nov. 18, 2014

(54) DRUG DELIVERY SYSTEM AND METHOD OF MANUFACTURING THEREOF

(75) Inventors: Sean R. Kirkpatrick, Littleton, MA (US); Richard C. Svrluga, Newton, MA (US)

(73) Assignee: Exogenesis Corporation, Billerica, MA (US)

( * ) Notice: Subject to any disclaimer, the term of this patent is extended or adjusted under 35 U.S.C. 154(b) by 822 days.

This patent is subject to a terminal disclaimer.

(21) Appl. No.: 12/851,161

(22) Filed: Aug. 5, 2010

(65) Prior Publication Data

US 2011/0029068 A1 Feb. 3, 2011

Related U.S. Application Data (63) Continuation-in-part of application No. 11/550,069, filed on Oct. 17, 2006, now Pat. No. 7,923,055, which is a continuation-in-part of application No. 11/349,483, filed on Feb. 7, 2006, now Pat. No. 7,666,462, which is a continuation-in-part of application No. 10/144,919, filed on May 13, 2002, now Pat. No. 7,105,199, application No. 12/851,161, which is a continuation-in-part of application No. 12/210,018, filed on Sep. 12, 2008, now abandoned.

(60) Provisional application No. 60/290,389, filed on May 11, 2001, provisional application No. 60/317,652, filed on Sep. 6, 2001, provisional application No. 60/075,965, filed on Jun. 26, 2008, provisional application No. 60/972,663, filed on Sep. 14, 2007.

(51) Int. Cl.

| | |
|---|---|
| A61L 27/54 | (2006.01) |
| B05D 3/06 | (2006.01) |
| C23C 14/02 | (2006.01) |
| G21G 5/00 | (2006.01) |
| H01J 37/317 | (2006.01) |
| C23C 14/22 | (2006.01) |
| A61F 2/82 | (2013.01) |
| C23C 14/50 | (2006.01) |

(52) U.S. Cl.
CPC ....... *C23C 14/022* (2013.01); *A61F 2250/0067* (2013.01); *H01J 37/3171* (2013.01); *C23C 14/221* (2013.01); *A61F 2/82* (2013.01); *C23C 14/505* (2013.01); *H01J 2237/0812* (2013.01)
USPC ........... 424/423; 623/1.42; 427/2.1; 427/523; 250/492.3

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. | |
| 4,986,006 A | 1/1991 | Weaver | |
| 5,123,924 A | 6/1992 | Sioshansi et al. | |
| 5,133,757 A | 7/1992 | Sioshansi et al. | |
| 5,419,760 A | 5/1995 | Narciso | |
| 5,459,326 A | 10/1995 | Yamada | |
| 5,707,684 A * | 1/1998 | Hayes et al. | 427/162 |
| 5,763,504 A | 6/1998 | Matsuda et al. | |
| 5,814,194 A | 9/1998 | Deguchi et al. | |
| 5,843,172 A | 12/1998 | Yan | |
| 6,120,847 A | 9/2000 | Yang et al. | |
| 6,143,354 A | 11/2000 | Koulik et al. | |
| 6,156,373 A | 12/2000 | Zhong et al. | |
| 6,207,282 B1 | 3/2001 | Deguchi et al. | |
| 6,331,227 B1 | 12/2001 | Dykstra et al. | |
| 6,451,871 B1 | 9/2002 | Winterton et al. | |
| 6,486,478 B1 | 11/2002 | Libby et al. | |
| 6,491,800 B2 * | 12/2002 | Kirkpatrick et al. | 204/192.34 |
| 6,635,082 B1 | 10/2003 | Hossainy et al. | |
| 6,641,607 B1 | 11/2003 | Hossainy et al. | |
| 6,676,989 B2 * | 1/2004 | Kirkpatrick et al. | 427/2.28 |
| 6,716,444 B1 | 4/2004 | Castro et al. | |
| 6,746,773 B2 | 6/2004 | Llanos et al. | |
| 6,764,505 B1 | 7/2004 | Hossainy et al. | |
| 6,805,898 B1 | 10/2004 | Wu et al. | |

(Continued)

FOREIGN PATENT DOCUMENTS

| | | |
|---|---|---|
| JP | 10-66721 A | 10/1998 |
| WO | 2007092894 A2 | 8/2008 |
| WO | 2009036373 A2 | 3/2009 |

OTHER PUBLICATIONS

International Search Report for PCT/US07/61787 dated Apr. 24, 2008.
Fehsenfeld P. et al., Production of Radioactive Stents:, Nachrichten Forschungszentrum Karlsruhe, 2000, pp. 81-86, vol. 32-1, Germany.
International Preliminary Report on Patentability for PCT/US07/61787 dated Aug. 21, 2008.
Matsuo, J. et al. What size of cluster is most appropriate for SIMS? Applied Surface Science 255 (2008) pp. 1235-1238.

*Primary Examiner* — Robert A Wax
*Assistant Examiner* — Danah Al-Awadi
(74) *Attorney, Agent, or Firm* — Burns & Levinson LLP; Jerry Cohen; David W Gomes (57) ABSTRACT

Irradiation of a surface of a material with a gas cluster ion beam modifies the wettability of the surface. The wettability may be increased or decreased dependent on the characteristics of the gas cluster ion beam. Improvements in wettability of a surface by the invention exceed those obtained by conventional plasma cleaning or etching. The improvements may be applied to surfaces of medical devices, such as vascular stents for example, and may be used to enable better wetting of medical device surfaces with liquid drugs in preparation for adhesion of the drug to the device surfaces. A mask may be used to limit processing to a portion of the surface. Medical devices formed by using the methods of the invention are disclosed.

19 Claims, 6 Drawing Sheets

(56) References Cited

U.S. PATENT DOCUMENTS

| | | | |
|---|---|---|---|
| 6,863,786 B2* | 3/2005 | Blinn et al. | 204/192.34 |
| 6,984,404 B1 | 1/2006 | Talton et al. | |
| 7,105,199 B2* | 9/2006 | Blinn et al. | 427/2.24 |
| 7,431,959 B1* | 10/2008 | Dehnad | 427/2.21 |
| 7,666,462 B2 | 2/2010 | Blinn et al. | |
| 2002/0017454 A1* | 2/2002 | Kirkpatrick | 204/192.34 |
| 2002/0139961 A1 | 10/2002 | Kinoshita et al. | |
| 2002/0188324 A1 | 12/2002 | Blinn et al. | |
| 2003/0009233 A1 | 1/2003 | Blinn et al. | |
| 2003/0143315 A1 | 7/2003 | Pui et al. | |
| 2005/0025804 A1 | 2/2005 | Heller | |
| 2005/0043787 A1 | 2/2005 | Kutryk et al. | |
| 2005/0244453 A1 | 11/2005 | Stucke et al. | |
| 2007/0087034 A1 | 4/2007 | Blinn et al. | |
| 2009/0036373 A1 | 2/2009 | Lang | |
| 2009/0074834 A1 | 3/2009 | Kirkpatrick et al. | |
| 2009/0098186 A1 | 4/2009 | Kirkpatrick et al. | |
| 2010/0098833 A1 | 4/2010 | Blinn et al. | |

* cited by examiner

DRUG DELIVERY SYSTEM AND METHOD OF MANUFACTURING THEREOF

CROSS-REFERENCE TO RELATED APPLICATIONS

This application is a Continuation-In-Part application of and claims the benefit of priority of co-pending U.S. patent application Ser. No. 11/550,069, filed Oct. 17, 2006 entitled "Drug Delivery System and Method of Manufacturing Thereof":

which claims the benefit of priority of U.S. patent application Ser. No. 11/349,483, filed Feb. 7, 2006 entitled "Drug Delivery System and Method of Manufacturing Thereof", now U.S. Pat. No. 7,666,462;

which claims the benefit of priority of U.S. patent application Ser. No. 10/144,919, filed May 13, 2002 and entitled "Method and System for Improving the Effectiveness of Medical Devices by Adhering Drugs to the Surface Thereof", issued as U.S. Pat. No. 7,105,199;

which claims the benefit of priority of U.S. Provisional Patent application Ser. Nos. 60/290,389, filed 11 May 2001, and 60/317,652, filed 6 Sep. 2001, each entitled "Method and System for Improving the Effectiveness of Medical Devices by Applying/Adhering Drugs to their Surface in Combination with the Application of Ion Beam Technology"; and each being hereby incorporated herein by reference in their entirety.

The present application also claims priority from U.S. patent application Ser. No. 12/210,018, filed Sep. 12, 2008 for "Method And System For Modifying The Wettability Characteristics Of A Surface Of A Medical Device By The Application Of Gas Cluster Ion Beam Technology And Medical Devices Made Thereby", which claims priority from U.S. Provisional Patent Application No. 61/075,965, filed Jun. 26, 2008 and entitled "Method And System For Modifying The Wettability Characteristics Of A Surface Of A Medical Device By The Application Of Gas Cluster Ion Beam Technology And Medical Devices Made Thereby", and from U.S. Provisional Patent Application No. 60/972,663 filed Sep. 14, 2007 and entitled "Method And System For Modifying The Wettability Characteristics Of A Surface Of A Medical Device By The Application Of Gas Cluster Ion Beam Technology And Medical Devices Made Thereby", the contents of all of which are hereby incorporated herein by reference in their entirety.

FIELD OF THE INVENTION

This invention relates generally to medical devices intended for implant in or to be in contact with a mammal and, more particularly to a method and system for modifying the surface of such medical devices by using gas cluster ion beam technology.

BACKGROUND OF THE INVENTION

Medical devices intended for implant into or for direct contact with the body of bodily tissues of a mammal (including a human), as for example medical prostheses or surgical implants, may be fabricated from a variety of materials including various metals, metal alloys, plastic or polymer materials, solid resin materials, glassy materials and other materials as may be suitable for the application and appropriately biocompatible. As examples, certain stainless steel alloys, cobalt-chrome alloys, polyethylene and other inert plastics have been used. Such devices include for example, without limitation, vascular stents, artificial joint prostheses, coronary pacemakers, implantable or contact lenses, etc. Often the native surface state of such a device has a wettability property that is other than ideal for the intended use. In such case it may be desirable to modify the wettability of at least a portion of such surfaces so as to make the surface wettability more suitable for the application or more suitable for other processing steps that ultimately make the surface more suitable for the application.

For example, in the case of an implantable vascular stent, it is often desirable to apply drugs to the surface of the stent prior to its introduction into a vascular vessel. When such drugs are applied in a liquid form, the wettability of the stent surface may affect the ability to apply a well-adhered drug layer. For another example, the degree of wettability of a surgical implant such as a joint prosthesis can affect the quality of lubrication that the joint enjoys after implant. As still another example, the wettability of a surface of a contact lens may affect the lubricity of the surfaces and the degree of wearer comfort.

Many materials have poorly wettable surfaces in their native states. Other materials have surfaces that become poorly wettable as a result of native oxides or other films that occur naturally after exposure to atmospheric conditions.

Many approaches have been applied in the past to affect the wettability of surfaces. These include the use of cleaning, including mechanical, ultrasonic, plasma, and chemical cleaning techniques. Other approaches have included the addition of surfactants or the application of films or coatings having different wettability characteristics. Often the cleaning and/or other measures have not been able to provide the desired results, or have been otherwise impractical, costly, undesirable, or ineffective. For many materials, cleaning alone is not adequate to provide wettability, since the native characteristics of the clean surface may not support wettability. For many materials, even an aggressive argon plasma surface cleaning does not provide suitable wettability of the material's surface.

Sometimes it is very useful that the wettability characteristics of a surface have a spatially variable quality. For example in the case of adhering a drug applied initially in a liquid form to surfaces of a surgically implantable medical device, it is sometimes useful to control the distribution of the drug on the surface so that portions of the surface have adhered drug, and other portions are substantially drug free—this may be done for therapeutic purposes or to minimize costs by not expending costly drugs on surface portions where there will be no useful effect.

Gas cluster ion beams are known, and have been used to process surfaces for purposes of cleaning, etching, smoothing, film growth, and the like. Gas cluster ions are ionized, loosely bound, aggregates of materials that are normally gaseous under conditions of standard temperature and pressure—typically consisting of from a few hundreds atoms or molecules to as many as a few ten thousands of atoms or molecules. Gas cluster ions can be accelerated by electric fields to considerable energies of thousands of keV. However because of the large number of atoms or molecules in each gas cluster ion, and because of the loose binding, their effect upon striking a surface is very shallow—the cluster is disrupted at impact and each atom or molecule carries only a few eV of energy. At the surface, instantaneous temperatures and pressures can be very high at gas cluster ion impact sites, and a variety of surface chemistry, etching, and cleaning effects can occur.

It is therefore an object of this invention to provide methods and systems for increasing the wettability of a surface of a medical device by the application of gas cluster ion beam technology.

Another object of this invention is to provide methods and systems for reducing the wettability of a surface of a medical device by the application of gas cluster ion beam technology.

Another object of this invention to provide methods and systems for modifying the wettability of a portion of a surface of a medical device in a controlled pattern by the application of gas cluster ion beam technology.

A still further object of this invention to provide methods and systems for improving the adherence of a coating originally applied in a fluid state to a surface of a medical device by improving the wettability of at least a portion of the surface by the application of gas cluster ion beam technology.

SUMMARY OF THE INVENTION

The objects set forth above as well as further and other objects and advantages of the present invention are achieved by the invention described hereinbelow.

The present invention applies gas cluster ion beam (GCIB) processing of a surface to modify its surface properties including the degree of wettability of the surface. Through the use of masking techniques or by controlling the incidence of the GCIB onto the surface or by other means of controlling the spatial extent of the GCIB processing, the surface characteristics may be modified in a controlled pattern with desired regions modified and other regions unmodified. A mask employed for controlling the spatial extent of GCIB processing may be either a contact mask or a non-contact mask. Photolithography techniques may be employed.

The inventors have found that processing surfaces with GCIB prior to the application of drug substances, makes those surfaces more electrically active.

The inventors have processed surfaces of a variety of materials with various GCIB techniques and have found that certain types of GCIB processing result in increasing the wettability of various materials and that other types of GCIB processing result in decreasing the wettability of various materials. By comparing the results to plasma cleaning techniques, it is shown by the inventors that in the increased wettability cases, the result is more effective than plasma cleaning and thus represents a surface modification that is not a result of just cleaning of the surface. Inert gas (such as argon (Ar)) GCIB processing and methane ($CH_4$) GCIB processing tends to increase the wettability characteristics of many surfaces. GCIB processing using oxygen-containing, nitrogen-containing, and other chemically reactive beams often decreases the wettability of the surfaces of many materials (despite the fact that those beams also clean the surfaces).

Without wishing to be bound to a specific theory, it may be that certain GCIB processes tend to remove native oxides and other thin films and further passivate the surfaces in such a way to improve wettability and to retard regrowth of anti-wettability films, while certain other GCIB processes may tend to chemically react the surfaces in such a way as to produce anti-wettability surface films.

To produce patterned surface wettability variations, the GCIB processing may be controlled using masks or beam writing techniques, or other means for controlling the exposure of the workpiece surfaces to GCIB processing in such a way as to restrict processing to certain regions of the surface or to produce differing types of GCIB processing in differing regions of the workpiece. Masks employed may be mechanical masks that shadow portions of the workpiece from GCIB processing or may employ photolithographic masking techniques, or may employ application of conformal or elastic masks to effectively mask non-planar workpieces, thus controlling the regions of GCIB processing.

In one embodiment, a method of applying a drug to a surface of a medical device comprises the steps of forming a gas cluster ion beam, irradiating at least some of the surface with the gas cluster ion beam to modify the wettability thereof, and applying a drug containing liquid to the surface so as to coat at least a portion of the surface of the medical device with the drug containing liquid.

The method may further comprise the step of drying the liquid from the surface to leave the drug subsequent to the applying step. The method may further comprise the steps of forming a second gas cluster ion beam, and irradiating the drug and the surface of the medical device with the second gas cluster ion beam to adhere the drug to the surface of the medical device and/or to modify an elution property of the drug.

The step of irradiating may include applying a patterned mask, having openings, to a portion of the surface prior to irradiating the surface, irradiating a specific portion of the surface through the openings in the patterned mask with the gas cluster ion beam to modify the wettability of the specific portion of the surface, and removing the patterned mask. The method may further comprise the step of repeating the applying, irradiating and removing steps prior to the applying step.

The surface may comprise a metal, a ceramic, a glassy material, a solid resin, a polymer, a copolymer, a stainless steel alloy, titanium, a titanium alloy, a metal oxide, poly (tetrafluoroethene), poly(tetrafluoro ethylene), perfluoro-alkoxy, hexafluoropropylene-tetrafluoroethylene copolymer, polycarbonate, an acrylic polymer, polymethylmethacrylate, a silicone, or silicone acrylate.

A medical device may be created with a drug coating formed by the above method.

A vascular stent may be created with an adhered drug, formed by the above method.

In another embodiment, a method of modifying the wettability of a surface comprises the step of irradiating at least a portion the surface with a gas cluster ion beam. The surface wettability may be increased or decreased. The gas cluster ion beam may comprise an inert gas and/or methane. The inert gas may be argon.

The gas cluster ion beam may comprise a reactive element, oxygen or nitrogen. The surface may be a surface of a medical device, a surface of a vascular stent, a surface of a lens or a surface of a prosthetic device. The step of irradiating may include providing a patterned mask for masking a portion of the surface, to prevent irradiation of the masked portion.

In yet another embodiment, a method for applying a solid material to a surface, comprises the steps of irradiating the surface with a gas cluster ion beam to modify the wettability of the surface, applying the solid material to the surface in a liquid suitable for physical affiliation with at least a portion of the surface having a higher wettability, and drying at least some of the liquid from the surface to leave the solid material in place on the surface.

The method may further comprise irradiating the solid material on the surface to improve bonding there between. The solid material may be carried in the liquid as a solution and/or a suspension. The method may further comprise a first step of cleaning the surface, prior to the step of irradiating, which first step of cleaning may decrease wettability of the surface.

For a better understanding of the present invention, together with other and further objects thereof, reference is made to the accompanying drawings and detailed description and its scope will be pointed out in the appended claims.

DETAILED DESCRIPTION OF THE PREFERRED METHODS AND EMBODIMENTS

Figure 1:
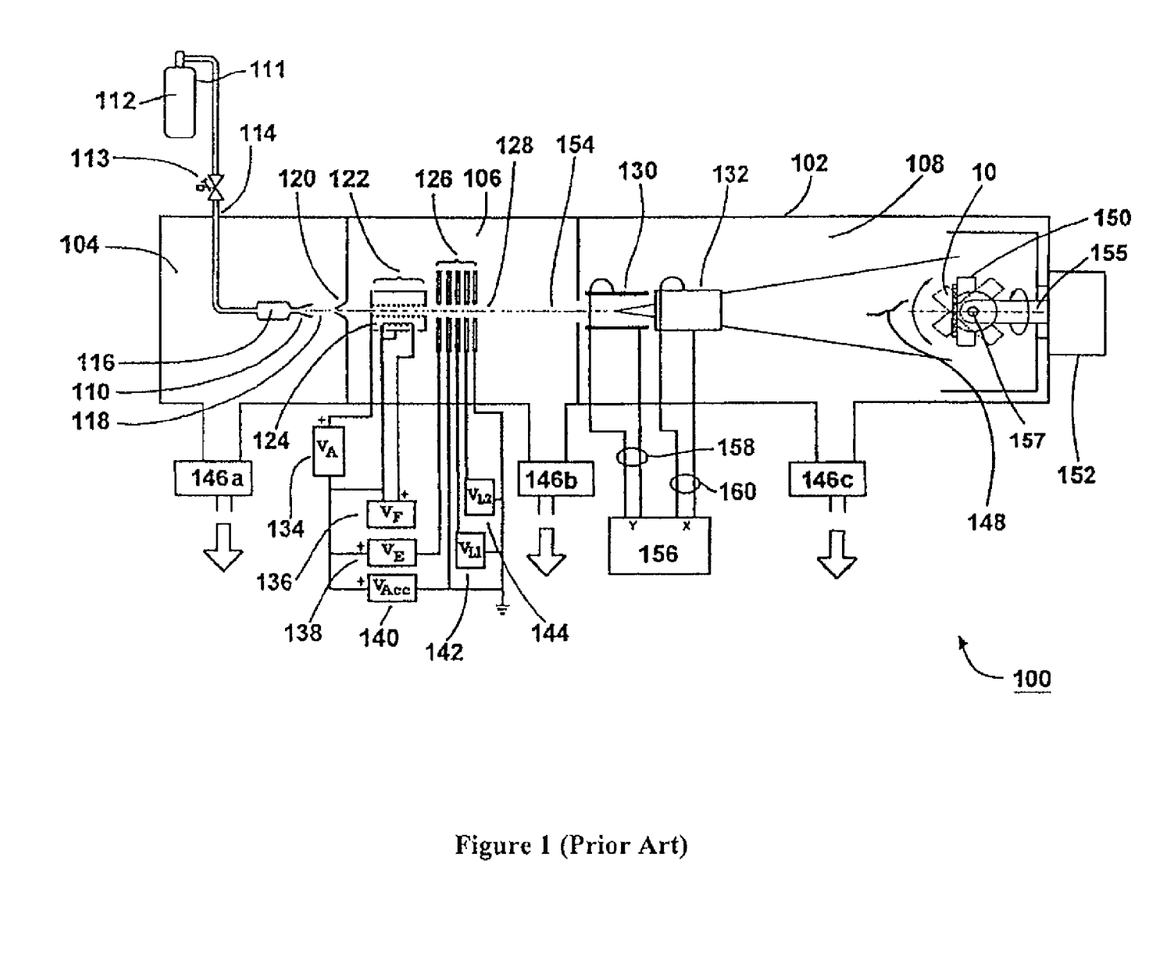
FIG. 1 is a schematic view of a gas cluster ion beam processing system of a type known in the GCIB art.

Reference is made to FIG. 1 of the drawings, which shows a typical gas cluster ion beam (GCIB) processor 100 of a type known in prior art for surface processing. Although not limited to the specific components described herein, the processor 100 is made up of a vacuum vessel 102 which is divided into three communicating chambers, a source chamber 104, an ionization/acceleration chamber 106, and a processing chamber 108 which includes therein a workpiece holder 150 capable of positioning a workpiece 10 for processing by a gas cluster ion beam.

During use, the three chambers are evacuated to suitable operating pressures by vacuum pumping systems 146a, 146b, and 146c, respectively. A condensable source gas 112 (for example argon or $N_2$) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, most consisting of from a few hundred to several thousand (or even tens of thousands) weakly bound atoms or molecules. A gas skimmer aperture 120 partially separates the gas molecules that have not condensed into a cluster from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to inert gases (such as argon), nitrogen, carbon dioxide, and oxygen.

After the supersonic gas jet 118 containing gas clusters has been formed, the clusters are ionized in an ionizer 122. The ionizer 122 is typically an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion of the clusters to become positively ionized. A set of suitably biased high voltage electrodes 126 extracts the cluster ions from the ionizer 122, forming a beam, then accelerates the cluster ions with an acceleration potential (typically from 1 kV to as much as several tens of kV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{Acc}$ bias a high voltage electrode with respect to the ionizer 122 so as to result in a total GCIB acceleration potential equal to $V_{Acc}$ volts (V). One or more lens power supplies (142 and 144, for example) may be provided to bias high voltage electrodes with potentials ($V_{L1}$ and $V_{L2}$ for example) to focus the GCIB 128.

A workpiece 10 (which may for example be a medical device or a component of a medical device) to be processed by the GCIB processor 100 is held on a workpiece holder 150, disposed in the path of the GCIB 128. In order for uniform processing of the workpiece 10 to take place, the workpiece holder 150 is designed in a manner set forth below to appropriately manipulate workpiece 10, as may be required for uniform processing.

Figure 2:
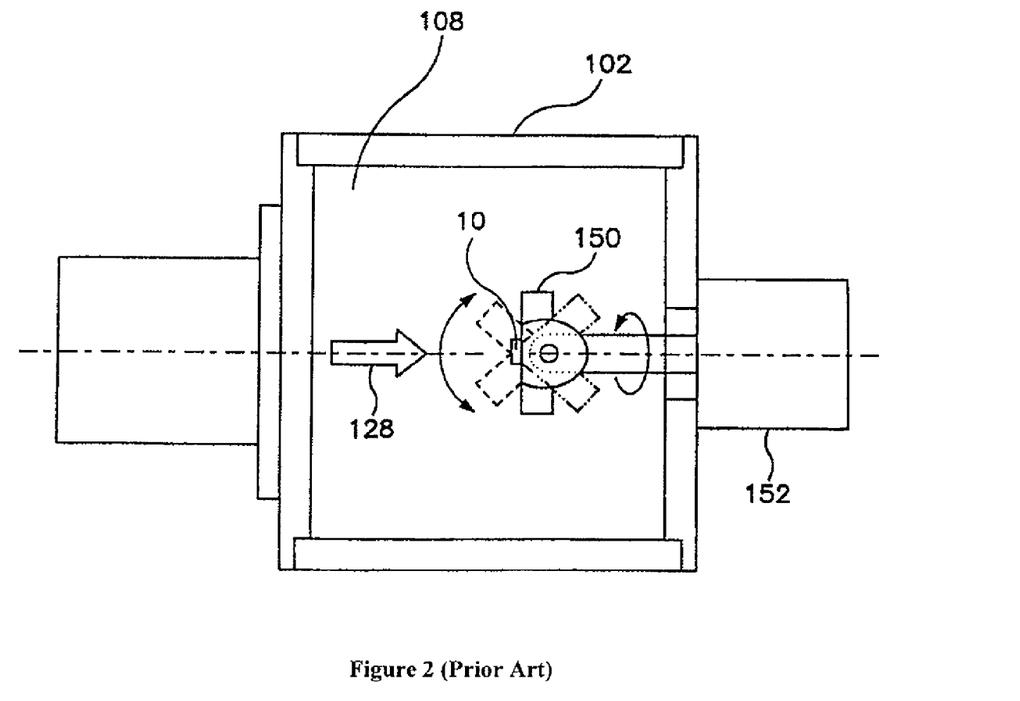
FIG. 2 is an enlarged view of a portion of the gas cluster ion beam processing system showing the workpiece holder.

Referring also to FIG. 2, any workpiece surfaces that are non-planar, that is may be of a spherical or cup-like or other un-flat configuration, may be oriented within a range of angles with respect to the beam incidence to obtain optimal GCIB processing of the workpiece surfaces. This employs a workpiece holder 150 with the ability to be fully articulated for orienting all non-planar surfaces to be processed in suitable alignment with the GCIB to provide processing optimization and uniformity. More specifically, when the workpiece 10 being processed is non-planar, the workpiece holder 150 is rotated and articulated by a mechanism 152 located at the end of the GCIB processor 100. The articulation/rotation mechanism 152 preferably permits 360 degrees of device rotation about longitudinal axis 155 (which may be coaxial with the initial trajectory 154 of the GCIB 128) and sufficient articulation about an axis 157 perpendicular to axis 155 to maintain the workpiece surface to within a desired range of beam incidence.

Under certain conditions, depending upon the size of the workpiece 10, a scanning system may be desirable to produce uniform smoothness. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the workpiece 10.

When beam scanning over an extended region is not desired, processing is generally confined to a region that is defined by the diameter of the beam. The diameter of the beam at the surface of the workpiece can be set by selecting the voltages ($V_{L1}$ and/or $V_{L2}$) of one or more lens power supplies (142 and 144 shown for example) to provide the desired beam diameter at the workpiece. Although not specifically shown, in FIGS. 1 and 2, such prior art GCIB processing systems typically employ sensors and circuits for measuring and controlling the GCIB parameters (as for example acceleration potential, beam current, beam focus, gas flow, beam dose applied to the workpiece, workpiece manipulation, etc.) important to processing and also employ additional controls and automation for automatic processing and processing recipe management, selection, and control.

Although FIGS. 1 and 2 show a workpiece holder and manipulator suitable for holding and manipulating certain types of planar and simply shaped non-planar workpieces, it will be understood by those familiar with the prior art that other types of simpler and more complex holders and manipulators are known. For example, U.S. Pat. No. 6,676,989 issued to Kirkpatrick et al. teaches a holder and manipulator optimized for processing tubular or cylindrical workpieces such as vascular stents. The contents of U.S. Pat. No. 6,676,989 are incorporated herein by reference. U.S. Pat. No. 6,486,478 issued to Libby et al. discloses a workpiece holder/manipulator adapted for loading and processing highly planar workpieces such as semiconductor wafers.

Figure 3:
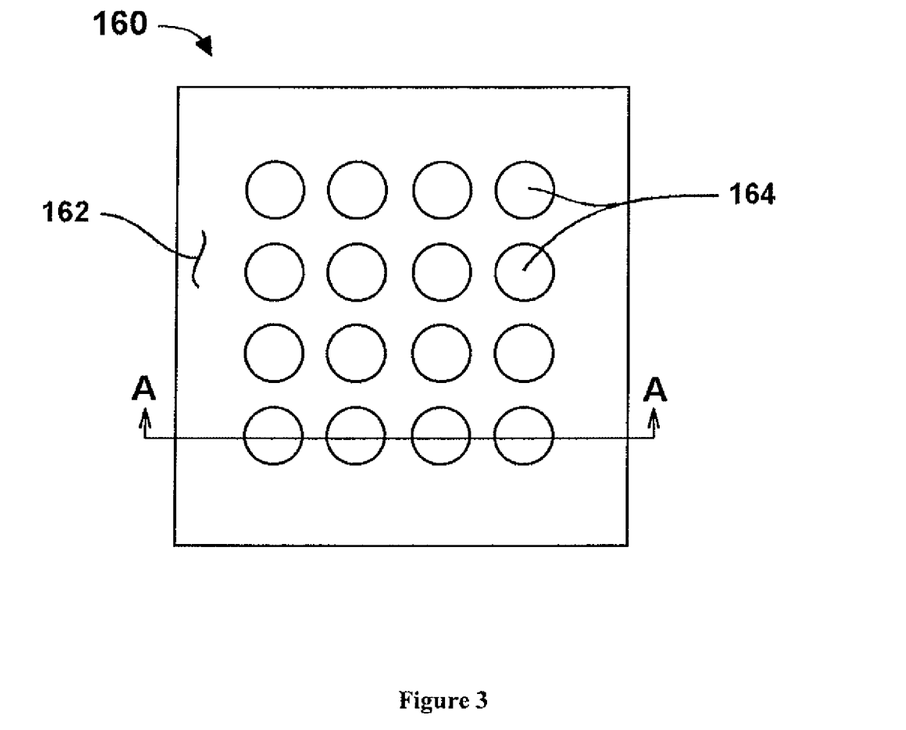
FIG. 3 is a schematic view of a metal mask used for controlling regions of processing by GCIB according to an embodiment of the invention.

FIG. 3 of the drawings shows a schematic view 160 of a metal mask 162 used for controlling regions of processing by GCIB according to an embodiment of the invention. The mask 162 is a rectangular aluminum plate having a multiplicity of holes 164 (two identified, for example) therein. The holes 164 penetrate the entire thickness of the mask 162. A section line A-A shows a virtual cutting plane for helping to understand FIG. 4.

Figure 4:
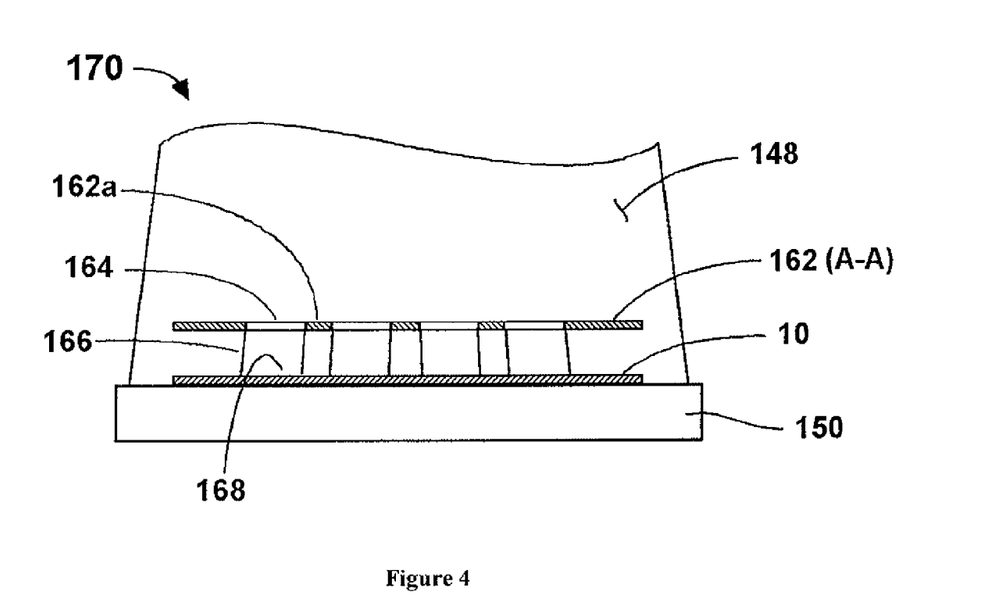
FIG. 4 is a schematic view showing use of the metal mask in controlling processing of a workpiece surface according to an embodiment of the invention.

FIG. 4 of the drawings is a schematic view 170 showing use of the metal mask 162 in controlling the GCIB processing of a workpiece surface according to an embodiment of the invention. The metal mask 162 is shown in side view as item 162 (A-A) at the virtual cutting plane A-A (indicated in FIG. 3). The metal mask is supported (support not shown) slightly above the workpiece 10, which is held on workpiece holder 150. A scanned GCIB 148 (partially shown) irradiates the metal mask 162, partially irradiates the workpiece 10, and partially irradiates the workpiece holder 150. Open holes 164 (for example) permit passage of the scanned GCIB 148 through the metal mask 162(A-A) at the holes 164. GCIB beamlets 166 (for example) that pass through the holes 164 irradiate the workpiece 10 at exposed regions 168 (for example) and process the workpiece to modify its wettability characteristics at the exposed regions (168) without affecting the workpiece in other regions that are masked by the lands 162a of the metal mask 162(A-A). As will be discussed hereinafter, the characteristics of the scanned GCIB 148 determine the effect of the GCIB beamlets 166 on the exposed regions 168.

Figure 5:
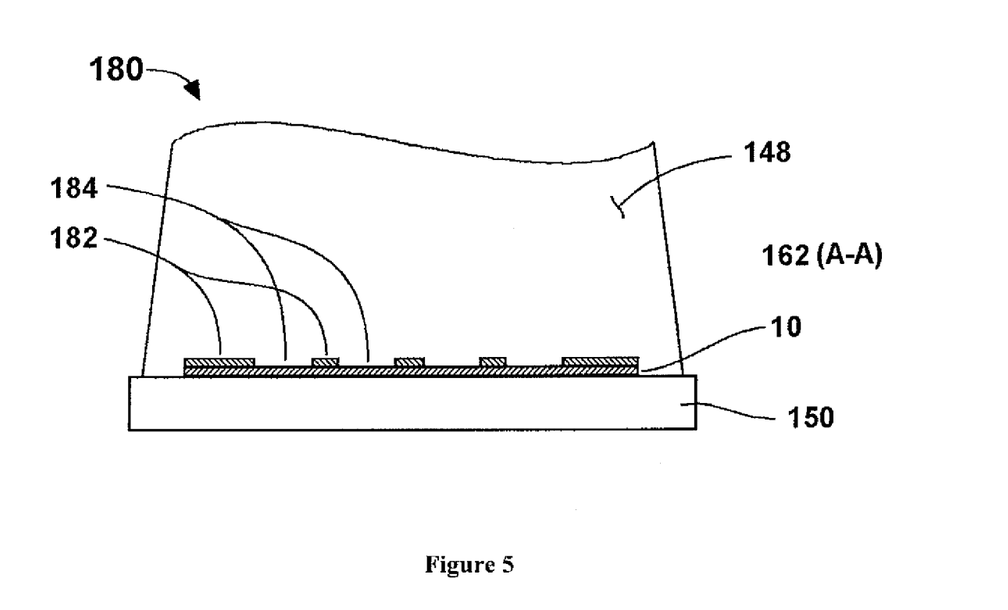
FIG. 5 is a schematic view showing the use of a photolithographic mask for controlling processing of a workpiece surface according to an embodiment of the invention.

FIG. 5 of the drawings is a schematic view 180 showing the use of a photolithographic mask for controlling processing of a workpiece 10 surface according to an embodiment of the invention. Using conventional photolithographic techniques, a photoresist layer may be applied to a surface of the workpiece 10. Conventional photo-exposure and developing techniques produce a patterned photoresist mask directly on a surface of the workpiece 10. Photoresist lands 182 (for example) mask the workpiece 10 from the scanned GCIB 148, while openings 184 (for example) in the photoresist permit the scanned GCIB 148 to irradiate the workpiece in the pattern exposed by the openings 184. Following GCIB processing of the workpiece, the photoresist lands 182 may be removed from the workpiece 10 surface using conventional techniques including but not limited to removal by solvents.

Figure 6:
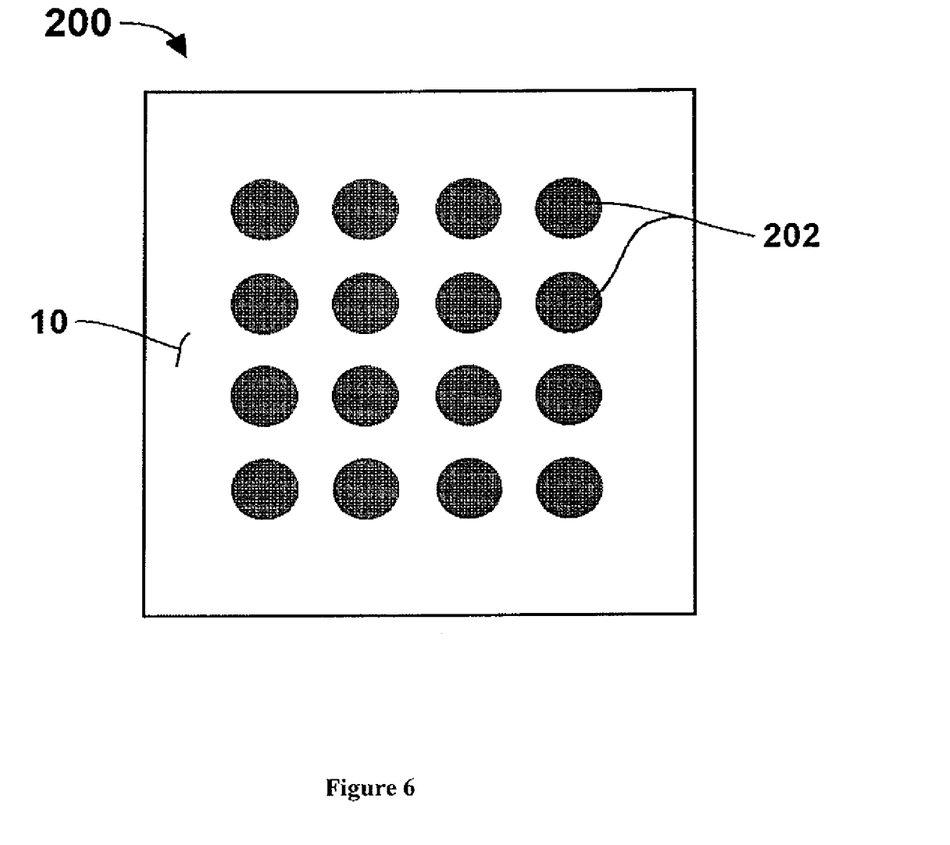
FIG. 6 is a drawing showing patterned wetting of a workpiece resulting from processing the workpiece using GCIB processing to improve wettability in a multiplicity of circular regions using a mask of the type shown in FIG. 4.

FIG. 6 is a drawing 200 showing patterned wetting of a workpiece as results from processing a workpiece using GCIB irradiation to increase the wettability in a multiplicity of regions 168 (FIG. 4) using a metal mask 162 (FIG. 4) of the type shown in FIG. 4. The workpiece 10 was a copper metal workpiece that prior to processing was substantially non-wettable. Following GCIB processing with a GCIB as described hereinbelow, the workpiece was dipped in pure de-ionized water and carefully examined. The circular regions 202 (for example) corresponding to the GCIB irradiated regions 168 (of FIG. 4) were readily wet by the atomized water and formed a clearly visible film of water, while in the un-irradiated regions of the surface of the copper workpiece 10, the water beaded with high contact angle and flowed off of the surface without wetting. Low power microscopic examination of the circular regions 202 confirmed that they were well wetted.

Tables 1 and 2 summarize results from evaluation of methods including exemplary methods of the invention to increase the wettability of various materials. Following conventional detergent cleaning, de-ionized water rinse, and drying, test coupons of various materials were processed using various selected processes to evaluate process ability to increase the wettability of the test coupons. Test coupon materials were stainless steel (SS), cobalt-chrome alloy (CoCr), copper (Cu), silicon (Si), and Mylar polyester (M), a polymer. All coupons exhibited a considerable degree of non-wettability following the detergent cleaning, rinse and drying. Table 1 summarizes results immediately after processing. Table 2 summarizes results at extended times after processing.

Various processes were applied to the test coupons and the coupons were then evaluated for wettability by de-ionized water.

Process 1: Coupons were placed in an argon plasma sputter coater operated in an etching mode with 400 V bias and a discharge current of 10 mA. Coupon surface exposure was 2.5 minutes operating at a pressure of 20 pascals.

Process 2: Coupons were irradiated by GCIB using an argon GCIB accelerated with an acceleration potential of 10 kV, receiving a total surface dose of $10^{15}$ gas cluster ions/cm$^2$.

Process 3: Coupons were irradiated by GCIB using an argon GCIB accelerated with an acceleration potential of 25 kV, receiving a total surface dose of $10^{15}$ gas cluster ions/cm$^2$.

Process 4: Coupons were irradiated by GCIB using an argon/methane mixture (2% methane) GCIB accelerated with an acceleration potential of 10 kV, receiving a total surface dose of $10^{15}$ gas cluster ions/cm$^2$.

Process 5: Coupons were irradiated by GCIB using an argon/methane mixture (2% methane) GCIB accelerated with an acceleration potential of 25 kV, receiving a total surface dose of $10^{15}$ gas cluster ions/cm$^2$.

TABLE 1

| | Wettability after Conventional Cleaning | Immediate Post-Process Wettability | | | | |
|---|---|---|---|---|---|---|
| Coupon Material | | Process 1 Argon Plasma Clean | Process 2 Ar GCIB 10 kV | Process 3 Ar GCIB 25 kV | Process 4 Ar—CH$_4$ GCIB 10 kV | Process 5 Ar—CH$_4$ GCIB 25 kV |
| SS | Nil | Poor | Good | Good | Good | Good |
| CoCr | Nil | Good | Good | Good | Good | Good |
| Cu | Nil | Good | Good | Good | Good | Good |

TABLE 1-continued

| Coupon Material | Wettability after Conventional Cleaning | Immediate Post-Process Wettability | | | | |
|---|---|---|---|---|---|---|
| | | Process 1 Argon Plasma Clean | Process 2 Ar GCIB 10 kV | Process 3 Ar GCIB 25 kV | Process 4 Ar—CH$_4$ GCIB 10 kV | Process 5 Ar—CH$_4$ GCIB 25 kV |
| Si | Nil | Good | Good | Good | Good | Good |
| M | Nil | Good | Good | Good | Good | Good |

TABLE 2

| Coupon Material | Process | Elapsed Time, Post-Process | | |
|---|---|---|---|---|
| | | Immediate | 1 day | 3 days |
| SS | 1 (Argon plasma clean) | Poor | Nil | Nil |
| | 2 (Ar GCIB 10 kV) | Good | Good | Nil |
| | 3 (Ar GCIB 25 kV) | Good | Slight | Nil |
| | 4 (Ar/ChH$_4$ GCIB 10 kV) | Good | Slight | Nil |
| | 5 (Ar/ChH$_4$ GCIB 25 kV) | Good | Good | Nil |
| CoCr | 1 (Argon plasma clean) | Good | Nil | Nil |
| | 2 (Ar GCIB 10 kV) | Good | Good | Nil |
| | 3 (Ar GCIB 25 kV) | Good | Good | Nil |
| | 4 (Ar/ChH$_4$ GCIB 10 kV) | Good | Slight | Slight |
| | 5 (Ar/ChH$_4$ GCIB 25 kV) | Good | Nil | Nil |
| Cu | 1 (Argon plasma clean) | Good | Nil | Nil |
| | 2 (Ar GCIB 10 kV) | Good | Good | Good |
| | 3 (Ar GCIB 25 kV) | Good | Nil | Nil |
| | 4 (Ar/ChH$_4$ GCIB 10 kV) | Good | Good | Nil |
| | 5 (Ar/ChH$_4$ GCIB 25 kV) | Good | Good-Slight | Slight |
| Si | 1 (Argon plasma clean) | Good | Nil | Nil |
| | 2 (Ar GCIB 10 kV) | Good | Good | Good |
| | 3 (Ar GCIB 25 kV) | Good | Good | Slight |
| | 4 (Ar/ChH$_4$ GCIB 10 kV) | Good | Good | Good |
| | 5 (Ar/ChH$_4$ GCIB 25 kV) | Good | Good | Good |
| M | 1 (Argon plasma clean) | Good | Good | Good |
| | 2 (Ar GCIB 10 kV) | Good | Good | Slight |
| | 3 (Ar GCIB 25 kV) | Good | Good | Good |
| | 4 (Ar/ChH$_4$ GCIB 10 kV) | Good | Good | Good |
| | 5 (Ar/ChH$_4$ GCIB 25 kV) | Good | Good-Slight | Slight |

Although argon plasma cleaning (Process 1) provided improved wettability immediately post-process, it only provided a lasting improvement in the case of the Mylar coupon. The GCIB Processes 2, 3, 4, and 5 always provided good wettability immediately post-processing, but furthermore continued to provide improved wettability over an extended period of time post-processing.

Additional experiments have shown that certain GCIB processing using source gases that comprise reactive atoms such as gas cluster ion beams formed from source gases containing oxygen or nitrogen tend to reduce the wettability of materials with good wettability. The mechanism is unknown, but a theory is that a surface film is formed by the GCIB irradiation that is an oxide, nitride, or other film that has properties that make it less wettable than the original surface of the material.

In the case of some medical devices, as for example some vascular stents, it is useful to coat the stent with a drug that inhibits restenosis of the stent-supported vascular vessel after stent insertion. It has been taught in U.S. Pat. No. 7,105,199 issued to Blinn et al., that when it is desired to adhere certain drugs to vascular stents for therapeutic purposes, such drugs may be applied to the cleaned stent in liquid form. After drying, according to U.S. Pat. No. 7,105,199 the drug may be irradiated by GCIB to bind it to the metal surface of the stent, resulting in a stent that retains the drug and elutes it slowly after insertion into a vascular vessel. A problem has been that in applying the liquid drug to the medical device (for example a vascular stent), lack of wettability of the medical device results in less retention of the drug on the medical device than is desirable. By applying the present invention to solution of the problem, medical devices with better drug adhesion can be obtained. First the bare medical device may be cleaned as in the prior art. Prior to application of the liquid drug, the medical device is treated by GCIB according to the method of this invention to improve its wettability. Next the liquid drug is sprayed onto the surface of the wettable medical device, resulting in better retention of and more uniform distribution of the drug on the medical device's surface. After drying, the dried, adhered drug film may be further processed by GCIB as in the prior art to further adhere it to the surface of the medical device and/or to modify the rate at which the drug elutes when the device is implanted in a mammal, resulting in a drug coated or drug eluting medical device with improved drug adhesion and/or better drug eluting properties.

In the case of some medical devices, it is desirable that only predetermined portions of the device should be coated with a drug, while other portions are best not drug coated. In such situations, liquid drug coating may be employed by treating a portion of the surface of the medical device to have increased wettability and/or treating another portion of the surface of the medical device to have reduced wettability. Thus application of the liquid drug adheres to the more wettable portion of the surface and does not adhere to the portion of the surface with reduced wettability. By applying the present invention to solution of the problem, medical devices with patterned drug attachment can be obtained. First the surface of the medical device may be cleaned as in the prior art. Prior to application of the liquid drug, the medical device is treated by one or more GCIBs, using one or more patterning masks and with cluster-ions selected to increase and/or decrease the surface wettability. Next the liquid drug is sprayed onto the surface of the medical device, where it adheres to the more wettable portions and does not adhere to the less wettable portions of the surface of the medical device. After drying, the dried, adhered drug film may be processed by GCIB as in the prior art to further adhere it to the stent surface and/or to modify the drug elution rate of the medical device, resulting in a patterned drug eluting stent with improved drug adhesion and/or modified drug eluting properties.

Another application of the invention is in the field of biochip micro-array fabrication in which selected region of a substrate (which may be, for example, silicon, glass, quartz, a portion of an active integrated electronic circuit, or a portion of a micromechanical device) is selectively coated in an array pattern with a number of different proteins, antibodies, chemical compounds, or DNA strands (in liquid form, solution, or suspension) and where it is desirable to promote the attachment of those materials to the substrate by controlling the wettability of the substrate in what may be a patterned manner.

Still another application is the application of paints or other coatings that are applied as a suspension in a liquid carrier to materials like plastics, polymers, glasses and other materials of low wettability. In such cases, the application of the GCIB technology of this invention can be effectively employed to form well-covered, well-adhered coatings on what are otherwise difficult to coat surfaces.

In many applications it is desirable to provide multi-layered coatings in patterned or un-patterned layers. The technology of this invention facilitates fabrication of a variety of useful devices that consist of multiple layers such as organic light emitting diode displays, biochips, semiconductor devices, solar cells, fuel cells, etc. Manufacturing of such devices begins with a substrate that (in the case of an organic light emitting diode (OLED) display, for example) may be glass or a plastic. An initial layer of an organic material in liquid form is applied to the substrate of an OLED display, which once it dries, may have hydrophobic qualities that may be detrimental to the formation of a subsequent layer of liquid material that is applied as the OLED display structure is built. To overcome this problem, prior art manufacturing may use wet chemistry to modify the surface wettability of the first applied layer in order to obtain a wettable surface for subsequent coating. Such wet chemistry can damage the initial layer and can be difficult to control. GCIB processing according to the present invention is a preferable alternative to such wet chemistry in that each successive layer may have its wettability modified to make it uniformly wettable or wettable in a specifically masked pattern to form a suitable substrate for successively applied liquid coatings. The ability to produce surfaces with wettability carefully tailored in such a controlled fashion is beneficial to the manufacture of a variety of layered devices, wherein the layering is dependent on providing multiple sequential coatings applied in liquid form and wherein one or more of the coatings dries with poor wettability properties.

In addition to non-biological materials, it is also possible to modify the wettability of surfaces of materials of biological origin with GCIB processing and such modification can be beneficially employed in situations like surgical implantation of such materials where increased wettability may result in improved implant success, lower rejection rate, or improved ability to attach drugs to the surfaces of the biological materials. Although the invention has been described with respect to various embodiments comprising medical devices, it will be realized by those skilled in the arts that though the invention is particularly useful for managing the wettability of surfaces of medical devices it is not limited to application to medical devices and may be applied to a wide range of articles and devices for which controlled and/or patterned surface wettability is desired or advantageous.

Although the invention has been described with respect to controlling and/or patterning surface wettability of various materials including stainless steel, cobalt-chrome alloy, copper, silicon, and the polymer Mylar polyester, it is also applicable to a wide range of other material surfaces including, but not limited to, ceramics, metal oxides (including oxides of titanium, and oxides of other metals), other metals (including titanium and titanium alloys), and other polymers and copolymers, including poly(tetrafluoroethene), poly(tetrafluoroethylene), perfluoroalkoxy, hexafluoropropylene-tetrafluoro ethylene copolymer, polycarbonate, acrylic polymers, polymethylmethacrylate, silicones, and silicone acrylate. Although the invention has been described with respect to the application of GCIBs having clusters comprising various gases, it will be realized by those skilled in the art that other constituent gases may also be beneficially employed. These include the noble gases, Ne, Ar, Xe, and other reactive gases, including without limitation, reactive gases comprising atoms of reactive elements including the halogens, oxygen, and nitrogen, and other carbon-containing gases, both organic and inorganic. Although the invention has been described with to the application of GCIBs having clusters of mixed composition comprising various mixed gases, it will be realized by those skilled in the art that other mixtures of constituent gases may be beneficially employed. These included mixtures having two or more components from the groups consisting of noble gases, carbon-containing gases, and reactive gases. It should be realized this invention is also capable of a wide variety of further and other embodiments within the spirit and scope of the foregoing disclosure and the appended claims.

What is claimed is:

1. A method of applying a drug to a surface of a medical device comprising the steps of:
    forming a gas cluster ion beam;
    irradiating at least some of the surface with the gas cluster ion beam to modify the wettability thereof; and
    applying a drug containing liquid to the surface so as to coat at least a portion of the surface of the medical device with the drug containing liquid.

2. The method of claim 1, further comprising the step of drying the liquid from the surface to leave the drug subsequent to the applying step.

3. The method of claim 2, further comprising the steps of;
    forming a second gas cluster ion beam; and
    irradiating the drug and the surface of the medical device with the second gas cluster ion beam to adhere the drug to the surface of the medical device and/or to modify an elution property of the drug.

4. The method of claim 1, wherein the step of irradiating includes
    applying a patterned mask, having openings, to a portion of the surface prior to irradiating the surface;
    irradiating a specific portion of the surface through the openings in the patterned mask with the gas cluster ion beam to modify the wettability of the specific portion of the surface; and
    removing the patterned mask.

5. The method of claim 4, further comprising the step of repeating the applying,
    irradiating and removing steps prior to the applying step.

6. The method of claim 1, wherein the surface comprises a metal, a ceramic, a glassy material, a solid resin, a polymer, a copolymer, a stainless steel alloy, titanium, a titanium alloy, a metal oxide, poly(tetrafluoroethene), poly(tetrafluoroethylene), perfluoroalkoxy, hexafluoropropylene-tetrafluoroethylene copolymer, polycarbonate, an acrylic polymer, polymethylmethacrylate, a silicone, or silicone acrylate.

7. A medical device with a drug coating formed by the method of claim 1.

8. A vascular stent with adhered drug, formed by the method of claim 3.

9. A method of modifying the wettability of a surface comprising the step of irradiating at least a portion the surface with a gas cluster ion beam, wherein the gas cluster ion beam comprises methane.

10. The method of claim 9, wherein the surface wettability is increased or decreased.

11. The method of claim 10, wherein the gas cluster ion beam comprises an inert gas and methane.

12. The method of claim 11, wherein the inert gas is argon.

13. The method of claim 10, wherein the gas cluster ion beam comprises a reactive element.

14. The method of claim 9, wherein the surface is a surface of a medical device, a surface of a vascular stent, a surface of a lens or a surface of a prosthetic device.

15. The method of claim 9, wherein the step of irradiating includes providing a patterned mask for masking a portion of the surface, to prevent irradiation of the masked portion.

16. A method for applying a solid material to a surface, comprising the steps of:
   irradiating the surface with a gas cluster ion beam to modify the wettability of the surface;
   applying the solid material to the surface in a liquid; and
   drying at least some of the liquid from the surface to leave the solid material in place on the surface.

17. The method of claim 16, further comprising irradiating the solid material on the surface to improve bonding there between.

18. The method of claim 16, wherein the solid material is carried in the liquid as a solution and/or a suspension.

19. The method of claim 16, further comprising a first step of cleaning the surface prior to the step of irradiating.

* * * * *